United States Patent
Butler

(10) Patent No.: US 7,367,342 B2
(45) Date of Patent: May 6, 2008

(54) WOUND MANAGEMENT SYSTEMS AND METHODS FOR USING THE SAME

(75) Inventor: Glenn Butler, Tarrytown, NY (US)

(73) Assignee: Life Support Technologies, Inc., Tarrytown, NY (US)

( * ) Notice: Subject to any disclaimer, the term of this patent is extended or adjusted under 35 U.S.C. 154(b) by 693 days.

(21) Appl. No.: 10/726,028

(22) Filed: Dec. 2, 2003

(65) Prior Publication Data

US 2004/0193218 A1    Sep. 30, 2004

Related U.S. Application Data

(60) Provisional application No. 60/430,243, filed on Dec. 2, 2002.

(51) Int. Cl.
*A61B 19/00*    (2006.01)
*A61B 18/18*    (2006.01)

(52) U.S. Cl. .............................. 128/898; 606/3; 606/9; 607/88

(58) Field of Classification Search ................ 128/898; 606/3, 4, 7–15, 27; 607/88, 89, 92–94, 96, 607/100

See application file for complete search history.

(56) References Cited

U.S. PATENT DOCUMENTS

| | | | | |
|---|---|---|---|---|
| 5,026,367 | A | * | 6/1991 | Leckrone et al. ............... 606/7 |
| 5,041,108 | A | * | 8/1991 | Fox et al. ....................... 606/7 |
| 5,466,234 | A | * | 11/1995 | Loeb et al. .................... 606/15 |
| 5,573,531 | A | * | 11/1996 | Gregory ....................... 606/14 |
| 5,651,783 | A | * | 7/1997 | Reynard ........................ 606/4 |
| 5,725,522 | A | * | 3/1998 | Sinofsky ........................ 606/8 |
| 5,902,328 | A | * | 5/1999 | LaFontaine et al. ......... 607/116 |
| 6,152,919 | A | * | 11/2000 | Hakky .......................... 606/15 |
| 6,203,542 | B1 | * | 3/2001 | Ellsberry et al. ............. 606/41 |
| 6,605,082 | B2 | * | 8/2003 | Hareyama et al. ............ 606/11 |
| 6,979,328 | B2 | * | 12/2005 | Baerveldt et al. ............. 606/41 |
| 2003/0159700 | A1 | * | 8/2003 | Laufer et al. ................ 128/898 |

* cited by examiner

*Primary Examiner*—A. Farah
(74) *Attorney, Agent, or Firm*—Dugan & Dugan, P.C.

(57) ABSTRACT

In one aspect, a wound management system is provided. The wound management system includes a multi-lumen cannula adapted to be disposed in a wound site. The multi-lumen cannula includes (1) a fiber optic light distribution system adapted to irradiate the wound site with light; (2) one or more catheters adapted to deliver a fluid to the wound site; and (3) one or more evacuation lines adapted to remove fluid from the wound site. Numerous other aspects are provided.

5 Claims, 10 Drawing Sheets

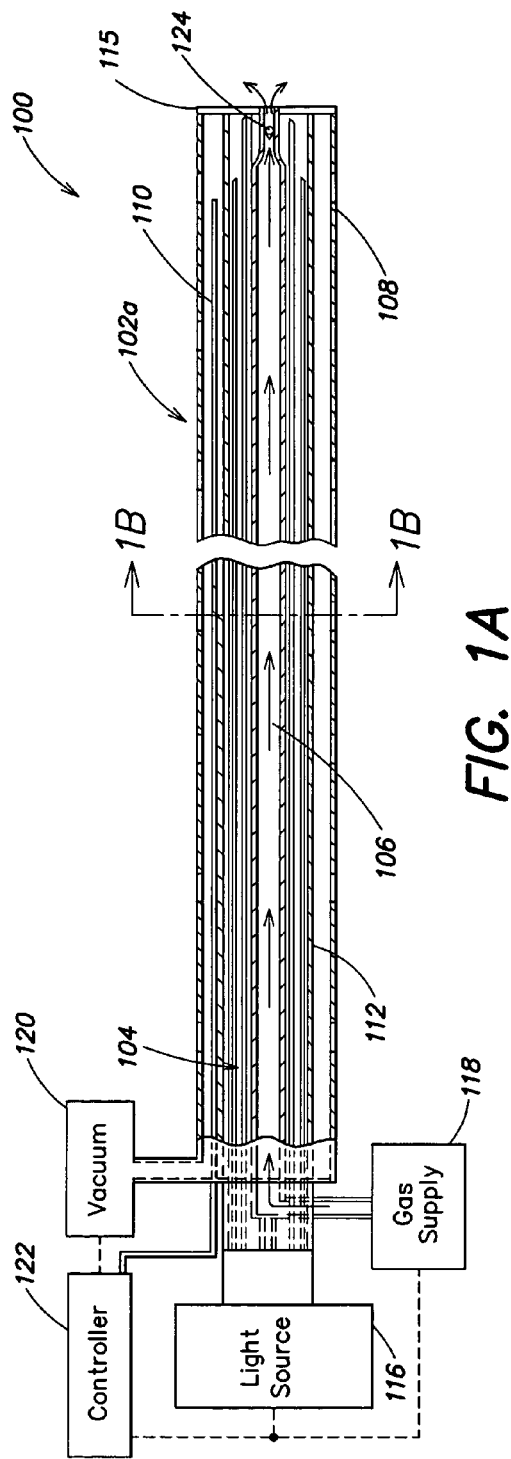
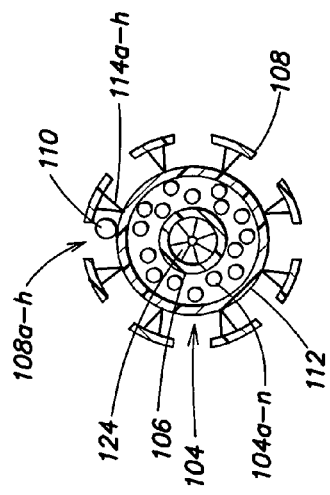
FIG. 1A
FIG. 1B

WOUND MANAGEMENT SYSTEMS AND METHODS FOR USING THE SAME

The present application claims priority from U.S. Provisional Patent Application Ser. No. 60/430,243, filed Dec. 2, 2002, which is hereby incorporated by reference herein in its entirety.

FIELD OF THE INVENTION

The present invention relates to medical treatments, and more specifically to wound management systems and methods for using such systems.

BACKGROUND OF THE INVENTION

The clinical management of decubitus, ischial and sacral ulcers represents one of the most difficult challenges to medical professional today. A stage-4 wound, for example, extends fully through soft tissue and often involves exposed bone and undermined surrounding tissue with significant sinus tracts that radiate out from the wound's epicenter. Such wounds usually have significant drainage, usually require daily dressing changes and are some of the most difficult and costly wounds to manage as patients are often bed ridden and very difficult to move.

The frequency of standard dressing changes for such wounds may range from a few times per day to several times per week, depending on wound drainage rate, healing rate, any infections, etc. In many cases, frequent (e.g., weekly) surgical debridement may be required to remove necrotic tissue and induce an inflammatory response necessary for new tissue granulation.

The frequency of dressing changes required during wound treatment has clear economic impacts. For example, under Medicare's new Prospective Payment System, visiting nurse services are paid a flat rate per month for patient home care regardless of the number of home visits required for dressing changes or other care. Accordingly, any new dressing system that can improve clinical efficacy and reduce the number of dressing changes required during wound treatment may not only improve patient care, but may potentially save millions of dollars annually.

To reduce the need for frequent dressing changes during treatment of draining wounds, drainage devices have been developed that utilize periodic suction and/or that generate a continuous negative pressure environment in a wound bed to express wound exudates (e.g., into a container), and thereby reduce dressing changes. While active exudate suctioning and a 100 to 150 mmHg negative pressure environment have been shown to improve wound closure as compared to atmospheric pressure wound management, such systems may infect a wound with airborne pathogens drawn into the wound via vacuum leaks in the wound dressing. Accordingly, an improved wound management system for treating wounds would be desirable.

SUMMARY OF THE INVENTION

In a first aspect of the invention, a first wound management system is provided. The first wound management system includes a multi-lumen cannula adapted to be disposed in a wound site and having (1) a fiber optic light distribution system adapted to irradiate the wound site with light; (2) one or more catheters adapted to deliver a fluid to the wound site; and (3) one or more evacuation lines adapted to remove fluid from the wound site. The first wound management system further includes a light source coupled to the fiber optic light distribution system, and adapted to supply light to the fiber optic light distribution system. One or more fluid supplies are coupled to the one or more catheters, and are adapted to supply fluid to the one or more catheters. A vacuum system is coupled to the one or more evacuation lines, and is adapted to evacuate the one or more evacuation lines. The first wound management system also includes a controller coupled to the light source, the one or more fluid supplies and the vacuum system. The controller is adapted to (1) employ the vacuum system to remove exudates from the wound site; (2) employ the one or more catheters to deliver fluid to the wound site; and (3) employ the light source to deliver at least one light dose to the wound site.

In a second aspect of the invention, a second wound management system is provided. The second wound management system includes (1) one or more catheters adapted to deliver a fluid to a wound site; (2) one or more evacuation lines adapted to remove fluid from the wound site; (3) one or more fluid supplies coupled to the one or more catheters, and adapted to supply fluid to the one or more catheters; (4) a vacuum system coupled to the one or more evacuation lines, and adapted to evacuate the one or more evacuation lines; and (5) a controller coupled to the one or more fluid supplies and the vacuum system. The controller is adapted to employ the vacuum system to remove exudates from the wound site and employ the one or more catheters to deliver fluid to the wound site.

In a third aspect of the invention, a third wound management system is provided. The third wound management system includes a multi-lumen cannula adapted to be disposed in a wound site. The multi-lumen cannula includes (1) a fiber optic light distribution system adapted to irradiate the wound site with light; (2) one or more catheters adapted to deliver a fluid to the wound site; and (3) one or more evacuation lines adapted to remove fluid from the wound site. Numerous other aspects are provided, as are methods and apparatus in accordance with these and other aspects of the invention.

Other features and aspects of the present invention will become more fully apparent from the following detailed description, the appended claims and the accompanying drawings.

BRIEF DESCRIPTION OF THE DRAWINGS

FIG. 1A is a first exemplary embodiment of a wound management system provided in accordance with the present invention.

FIG. 1B is a cross sectional view of the multi-lumen lumen cannula of FIG. 1A taken along line 1B-1B in FIG. 1A.

DETAILED DESCRIPTION

Figure 2:
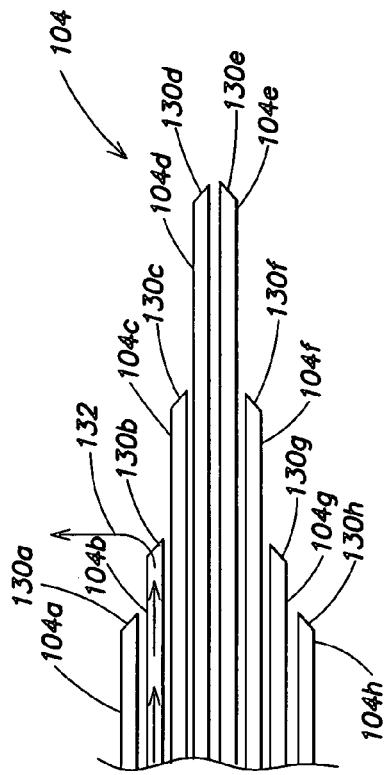
FIG. 2 is a schematic diagram of an exemplary embodiment of the fiber optic light distribution system of FIGS. 1A and 1B.

Large area chronic wounds such as decubitus, ischial and sacral ulcers generally require a dynamic environment in order to maintain an inflammatory process following surgical debridement. However, conventional dressings and treatment systems that employ active exudate suctioning and/or negative pressure environments tend to create static wound environments where marginal tissues fail, and colonized wounds tend to become infected if dressings are not changed frequently. In accordance with one or more embodiments of the present invention, methods, apparatus and systems are provided that can manage transient wound demands, such as through periodic suction of exudates, while supporting and maintaining other environmental parameters, such as controlled pressure, atmosphere, temperature, light dosing, etc., so as to maintain an inflammatory response that promotes tissue granulation with fewer dressing changes and lower cost.

FIG. 1A is a first exemplary embodiment of a wound management system 100 provided in accordance with the present invention. With reference to FIG. 1A, the wound management system 100 comprises a multi-lumen cannula 102a that contains a fiber optic light distribution system 104 (described below), a liquid and/or gas supply/return catheter 106, a wound exudate evacuation line 108 and a temperature measurement device (e.g., a thermistor 110). FIG. 1B is a cross sectional view of the multi-lumen cannula 102a of FIG. 1A taken along line 1B-1B in FIG. 1A. While only one supply/return catheter 106 and one wound exudate evacuation line 108 are shown in FIG. 1A, it will be understood that additional supply/return catheters and/or evacuations lines may be employed. For example, separate supply and/or return catheters may be employed for each gas or liquid to be supplied to a wound site (as described further below). More than one thermistor or other temperature measurement device also may be employed (as may be pressure and/or flow rate measurement devices).

With reference to FIG. 1B, the fiber optic light distribution system 104 includes a plurality of optical fibers 104a-n (contained within a fiber housing line 112) for delivering light to a wound site; and the wound exudate evacuation line 108 includes a plurality of intakes 108a-h for removing exudates from a wound site. One or more support members 114a-h, such as ridges or the like, may be disposed between the evacuation line 108 and the fiber housing line 112 to prevent the evacuation line 108 from collapsing when vacuum is applied to the evacuation line 108 (as described below). For example, a support member 114a-h may be positioned between each of the intakes 108a-h as shown in FIG. 1B. Few or more optical fibers 104a-n, intakes 108a-h and/or supports 114a-h than shown may be employed. An end cap or other similar mechanism 115 (e.g., a ball valve) may be coupled to a distal end of the multi-lumen cannula 102a (e.g., an end that extends into a wound site) so as to prevent exudate or other material from entering the fiber housing line 112. The end cap 115 may be removed, for example, to allow cleaning of the fiber optic light distribution system 104, the fiber housing line 112 and/or the evacuation line 108.

In the embodiment of the invention shown in FIG. 1A, the wound management system 100 also includes a light source 116 coupled to the fiber optic light distribution system 104, a gas supply 118 coupled to the supply/return catheter 106 and a vacuum system 120 (e.g., a conventional vacuum pump or the like) coupled to the wound exudate evacuation line 108. A controller 122 may be coupled to and control operation of the light source 116, the gas supply 118 and/or the vacuum system 120 as described below. The controller 122 also may be coupled to the thermistor 110 (e.g., for measuring a temperature of a wound site).

The supply/return catheter 106, the evacuation line 108 and/or the fiber housing line 112 each may comprise, for example, a section of suitable diameter flexible tubing (e.g., surgical silicone/rubber tubing, Teflon™, etc.). In one embodiment, the supply/return catheter 106 comprises approximately ¼ inch (outer diameter (O.D.)) flexible tubing, the fiber housing line 112 comprises approximately ⅜ inch O.D. flexible tubing and the evacuation line 108 comprises approximately ½ inch O.D. flexible tubing. Other tubing sizes may be employed for the supply/return catheter 106, the fiber housing line 112 and/or the evacuation line 108.

If the supply/return catheter 106 is employed primarily for supplying gas and/or liquid to a wound site, as shown in FIG. 1A, the supply/return catheter 106 may include a one-way valve 124 (e.g., a conventional check valve, such as a duck bill check valve, etc.) that (1) allows gas/liquid flow from the gas supply 118 through the supply/return catheter 106 to a wound site; and (2) prevents gas or liquid flow from the wound site back to the gas supply 118 through the supply/return catheter 106. Contamination of the supply/return catheter 106 (or any liquid or gas supply coupled thereto, such as the gas supply 118) thereby is prevented.

The light source 116 may comprise any light source suitable of supplying a dosage of light having one or more wavelengths and/or center frequencies to the fiber optic light distribution system 104 (e.g., one or more lasers, light emitting diodes, filtered white light sources, etc.). In one particular embodiment, the light source 116 comprises a plurality of lasers and/or light emitting diodes capable of delivering light with wavelengths ranging from about 350 nanometers to about 880 nanometers to the fiber optic light distribution system 104. Other wavelength ranges may be employed. In at least one embodiment of the invention, the controller 122 may direct the light source 116 to deliver one or more (controlled) doses of one or more wavelengths of light to a wound site via the fiber optic light distribution system 104.

The gas supply 118 may comprise a source of one or more gases such as oxygen, nitric oxide, carbon dioxide, etc. In at least one embodiment of the invention, the controller 122 may direct the gas supply 118 to deliver one or more gasses, or a combination thereof, to the return/supply catheter 106 (e.g., at a desired pressure and/or flow rate, for a desired time period, etc.).

The controller 122 may comprise, for example, one or more appropriately programmed microprocessors, microcontrollers, or the like. Alternatively, the controller 122 may comprise a dedicated hardware circuit, or a combination of hardware and software.

FIG. 2 is a schematic diagram of an exemplary embodiment of the fiber optic light distribution system 104 of FIGS. 1A and 1B. With reference to FIG. 2, the fiber optic light distribution system 104 comprises a plurality of optical fibers 104a-h. More or fewer optical fibers may be employed.

As shown in FIG. 2, each optical fiber 104a-h is cleaved or otherwise cut/configured so as to have an angled fiber/air interface 130a-h. Each angled fiber/air interface 130a-h is adapted to redirect (e.g., via refraction) light traveling within one of the optical fibers 104a-h radially away from the optical fiber and into a wound site (in which the fiber optic light distribution system 104 is employed). For example, depending on the index of refraction of the optical fiber 104a-h employed, a fiber/air interface 130a-h of about 45° (from the optical or central axis of the fiber) may refract light at an approximately 90° angle (from the optical or central axis of the fiber), as shown in FIG. 2 by light ray 132. Other fiber/air interface angles and/or angles of refraction may be employed. (In general, the fiber/air interfaces may be fiber/gas interfaces if other gas environments are employed.) Note that the optical fibers 104a-h may be "staggered" as shown to allow each fiber to transmit light energy into a wound site. Other configurations may be employed. In one embodiment, a 360° lateral light distribution is provided. Other types of light distribution may be provided.

Each optical fiber 104a-h may comprise any conventional optical fiber (e.g., a single node, multi-node, glass, plastic, etc., fiber). In at least one embodiment of the invention, each optical fiber 104a-h comprises a multi-mode, plastic optical fiber. Such plastic optical fibers typically are less likely to break if bent when compared to glass fibers. (Such bending may occur when the fiber optic light distribution system 104 is bent within a wound area as described further below). Further, plastic optical fibers typically are less efficient at transmitting light energy. Accordingly, such optical fibers may absorb light energy and generate heat during light transmission (thereby heating any gas being transmitted near the fiber optic light distribution system 104, such as gas being supplied to a wound sight through the supply/return catheter 106 of FIGS. 1A and 1B).

With reference to FIGS. 1A-2, the first wound management system 100 is adapted to perform numerous functions related to wound management. For example, the wound management system 100 (and/or other wound management systems described below) may:

(1) maintain a micro-ventilation (e.g., 10-100 cc/hour) of pure gas or a mixture of gases (e.g., pure oxygen, nitric oxide, carbon dioxide, combinations thereof, etc.) in a wound site per a predetermined and/or predefined protocol to help induce tissue growth, such as through use of the gas supply 118, the supply/return catheter 106, the evacuation line 108 and/or the vacuum system 120;

(2) temperature control gas supplied to a wound site to produce an ideal and/or controlled wound core temperature (e.g., about 100-101° F. in one embodiment); for example, wound bed temperature may be monitored (e.g., periodically or continuously) via the thermistor 110, and fed back to the controller 122; the controller 122 then may adjust gas supply temperature (e.g., via one or more heaters (not shown) coupled to the gas supply 118 and/or the supply/return catheter 106);

(3) produce short transient changes in pressure to remove exudates (e.g., pressure changes ranging from about 150 mmHg negative pressure), and/or longer term micro-hyperbaric granulation phase wound pressures (e.g., up to about 800 mmHg); for example, the controller 122 may control gas flow rate to a wound site via the gas supply 118 and/or gas exhaust rate from the wound site via the vacuum system 120 to achieve such pressure changes and/or pressures; one or more pressure measurement devices, such as a +/− pressure manometer, may be employed to monitored pressure within a wound site;

(4) provide dosed injection of liquids into a wound site (e.g., by permitting the injection of liquids such as saline, antibiotic solutions, coagulent solutions, etc., into the wound bed, allowing the solutions to diffuse within the wound bed, and then evacuating the solutions out of the wound bed); for example, the supply/return catheter 106, or another fluid delivery line, may be employed to deliver one or more liquids to a wound site (e.g., manually or via the controller 122), and the vacuum system 120/evacuation line 108 may be employed to remove the one or more injected liquids from the wound site (e.g., after a predetermined time period that may be set, for example, by the controller 122); and/or (5) employ the fiber optic light distribution system 104 to disperse light energy, preferably evenly, into the wound bed (e.g., at right angles to optical fibers 104a-h); preferably a broad range of wavelengths may be employed (e.g., ranging from at least UV-A (350 nm) to near infrared (880 nm)).

As described further below, a gas and/or liquid seal may be maintained around a wound site (e.g., employing a Tegaderm™ or similar material to form a gas/liquid seal) so as to maintain a sterile barrier and retain wound atmosphere and exudates within the wound site. In at least one embodiment, all gas and liquids are introduced to, and removed from a wound sight via the wound management system 100.

Figure 3A:
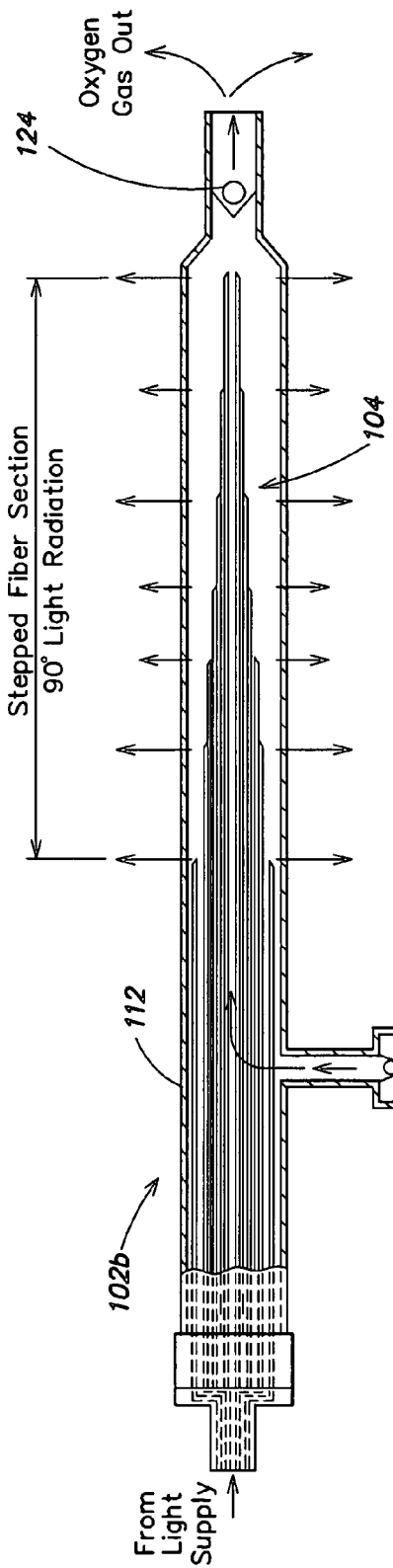
FIG. 3A is a schematic view of a first alternative embodiment of the multi-lumen cannula of FIG. 1A.

FIG. 3A is a schematic view of a first alternative embodiment of the multi-lumen cannula 102a of FIG. 1A, referred to as second multi-lumen cannula 102b in FIG. 3A. The second multi-lumen cannula 102b is similar to the multi-lumen cannula 102a of FIG. 1A, except that a separate supply/return catheter 106 is not employed in the multi-lumen cannula 102b of FIG. 3A. That is, within the multi-lumen cannula 102b of FIG. 3A, rather them employing a separate supply/return catheter 106, gas and/or liquids may be delivered to (and in certain embodiments removed from) a wound site through the fiber housing line 112. For clarity, the evacuation line 108 is not shown in the second multi-lumen cannula 102b. The second multi-lumen cannula 102b may employ a second check valve 140 (in addition to the first check valve 124) to further protect a gas or liquid supply from exudates or other unwanted contaminants that may be present in the fiber housing line 112. In at least one embodiment of the invention, an oxygen gas supply of 0.05-0.1 liters per minute (LPM) at 10 cm $H_2O$ pressure is employed. Other types of gas or liquid supplies may be employed. The second multi-lumen cannula 102b may be coupled to a light supply, for example, via a 4 mm ACMI connector or other suitable connector.

Figure 3B:
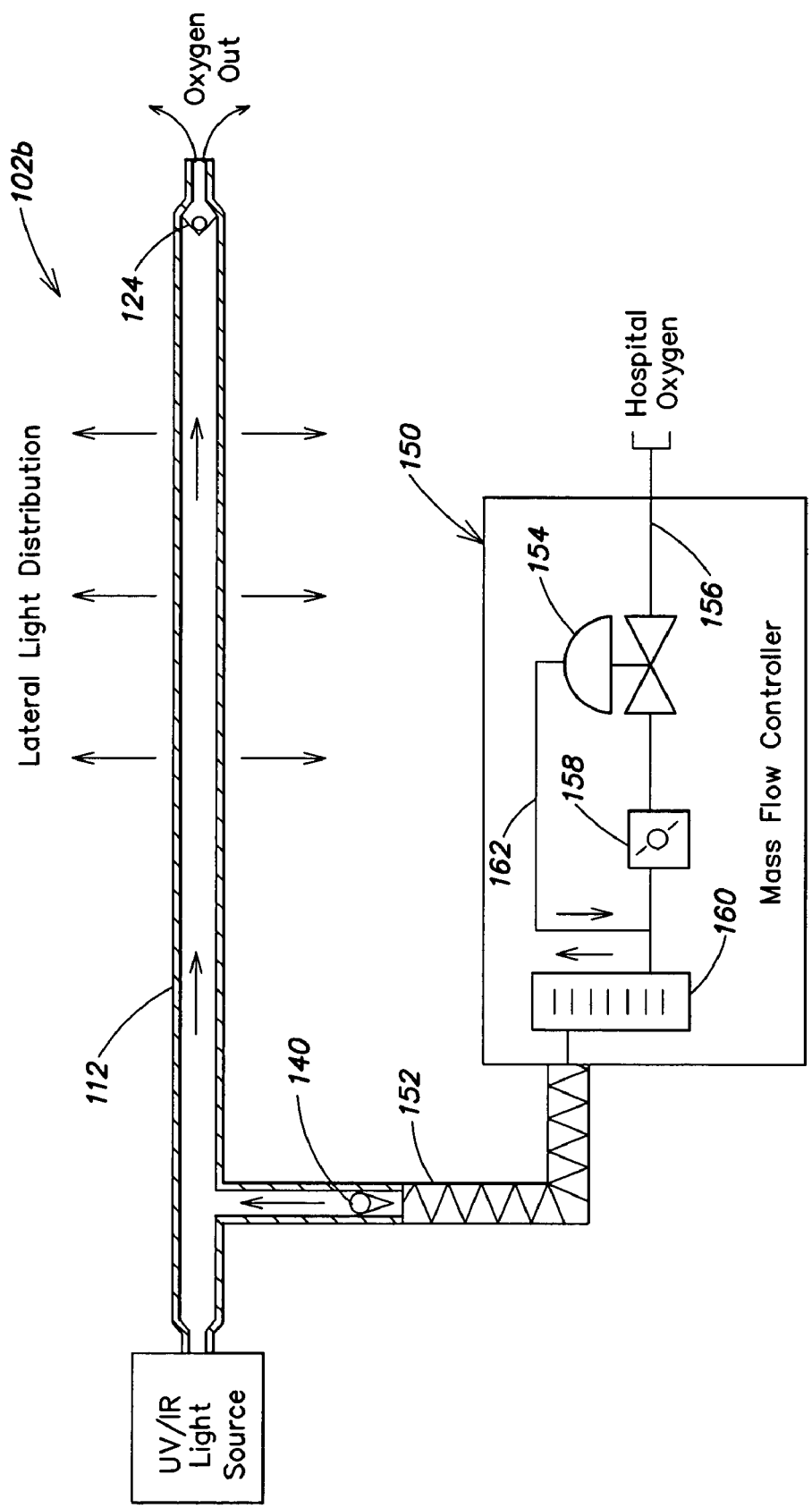
FIG. 3B is a schematic view of an embodiment of the second multi-lumen cannula of FIG. 3A wherein a hospital gas supply may be employed to deliver gas to a wound site.

FIG. 3B is a schematic view of an embodiment of the second multi-lumen cannula 102b of FIG. 3A wherein a hospital gas supply (not shown) may be employed to deliver gas (e.g., oxygen) to a wound site. With reference to FIG. 3B, a gas flow control system 150 is coupled to the fiber housing line 112 via a gas line 152 (e.g., a flexible gas line). The gas flow control system 150 is coupled to and receives gas flow from a hospital gas supply (such as a hospital oxygen supply, not shown). The light source may be coupled to the fiber housing line 112 via a fiber gas seal. Any suitable seal may be employed.

With reference to FIG. 3B, the gas flow control system 150 includes a pneumatically controlled valve 154 adapted to couple to the hospital gas supply (not shown, such as a 50 PSIG or other suitable pressure supply) via a gas line 156, a fixed orifice 158 coupled to the gas line 156 downstream from the valve 154 and a flow meter 160 coupled to the gas line 156 downstream from the fixed orifice 158. The valve 154, the gas line 156, the fixed orifice 158 and the flow meter 160 may comprise any suitable conventional components. In operation, gas is supplied to the gas line 156 from the hospital gas supply (not shown) and flows into the gas line 156, through the valve 154, through the fixed orifice 158 and through the flow meter 160 into the fiber housing line 112 of the multi-lumen cannula 102b. A feedback path 162 coupled between the output of the fixed orifice 158 and the valve 154 allows the pressure at the downstream side of the fixed orifice 158 to control opening and closing of the valve 154. That is, as the pressure at the downstream side of the fixed orifice 158 increases, the valve 154 opens; and as the pressure at the downstream side of the fixed orifice 158 decreases, the valve 154 closes. An approximately constant differential pressure thereby is maintained across the fixed orifice 158 regardless of variations in supply pressure. A constant flow rate of gas to the fixed housing line 112 thereby is assured. Other techniques for controlling pressure flow to the multi-lumen cannula 102b (or any other cannula described herein) may be employed (e.g., other than a fixed-orifice downstream mass flow controller); and the gas flow control system 150 may be employed with any of the cannula described herein.

Figure 4:
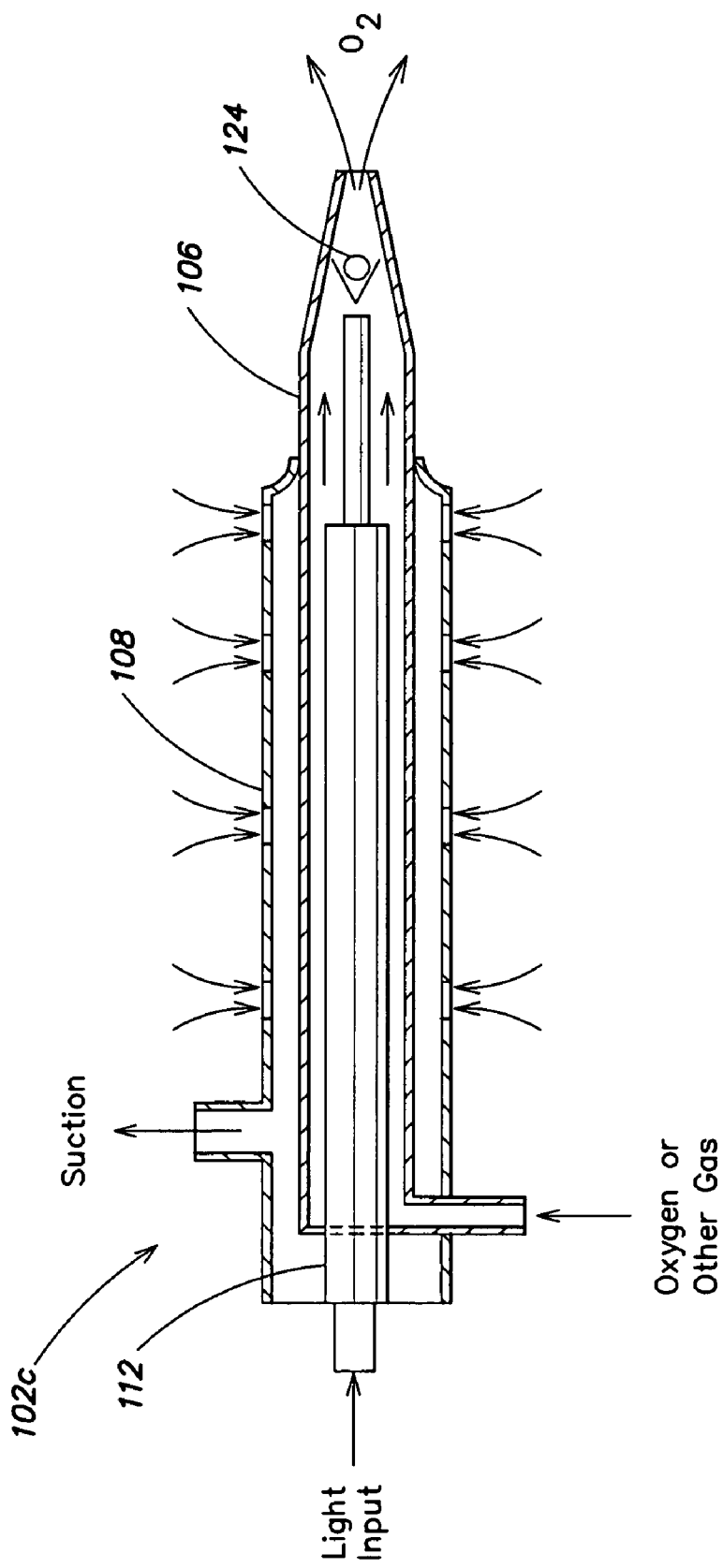
FIG. 4 is a schematic view of a second alternative embodiment of the multi-lumen cannula of FIG. 1A.

FIG. 4 is a schematic view of a second alternative embodiment of the multi-lumen cannula 102a of FIG. 1A, referred to as third multi-lumen cannula 102c in FIG. 4. The third multi-lumen cannula 102c is similar to the multi-lumen cannula 102a of FIG. 1A, except that the supply/return catheter 106 has a larger diameter than the fiber housing line 112. In one exemplary operation, the third multi-lumen cannula 102c may be employed to raise wound oxygen pressure to about +10 cm of $H_2O$ for twenty minutes and thereafter, to reduce the oxygen pressure to about −100 cm of $H_2O$ for five minutes. The above exemplary treatment process may be repeated. Other treatment processes may be employed.

Figure 5:
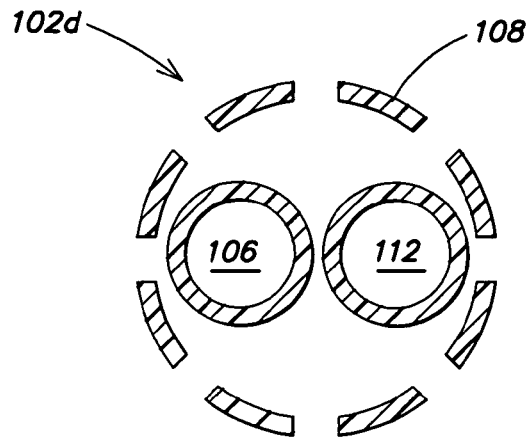
FIG. 5 is a front cross-sectional view of a third alternative embodiment of the multi-lumen cannula of FIG. 1A.

FIG. 5 is a front cross-sectional view of a third alternative embodiment of the multi-lumen cannula 102a of FIG. 1A, referred to as fourth multi-lumen cannula 102d in FIG. 5. The fourth multi-lumen cannula 102d is similar to the multi-lumen cannula 102a of FIG. 1A, except that the supply/return catheter 106 and the fiber housing line 112 are not concentric. Rather the supply/return catheter 106 and the fiber housing line 112 are positioned side-by-side within the evacuation line 108. In one exemplary embodiment, the supply/return catheter 106 and the fiber housing line 112 may have an outer diameter of about ⅛ to ⅜ inch, and the evacuation line 108 may have an outer diameter of about ½ inch or greater, although other dimensions may be employed. Note that the fiber optic light distribution system 104 alternatively may be housed within the supply/return catheter 106 and the additional line (fiber housing line 112) may be employed as another supply/return catheter. Also, the supply/return catheter 106 and the fiber housing line 112 may have different dimensions/diameters.

Figure 6:
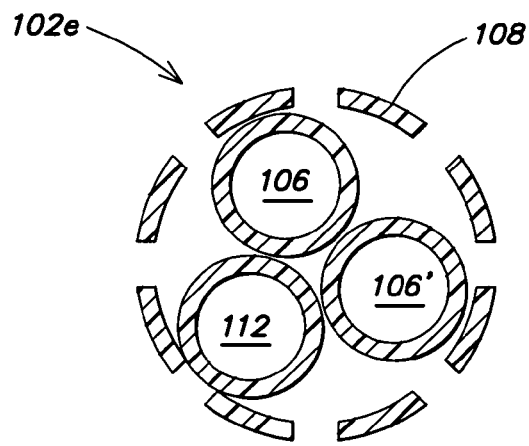
FIG. 6 is a front cross-sectional view of a fourth alternative embodiment of the multi-lumen cannula of FIG. 1A.

FIG. 6 is a front cross-sectional view of a fourth alternative embodiment of the multi-lumen cannula 102a of FIG. 1A, referred to as fifth multi-lumen cannula 102e in FIG. 6. The fifth multi-lumen cannula 102e is similar to the fourth multi-lumen cannula 102d of FIG. 5, except that the fifth multi-lumen cannula 102e includes an additional supply/return catheter 106'. Note that the supply/return catheters and/or the fiber housing line need not have the same dimensions/diameters.

Figure 7:
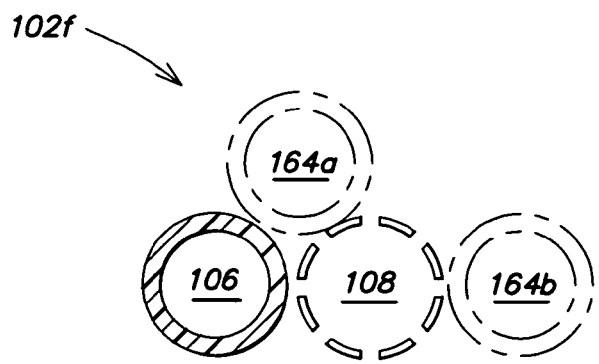
FIG. 7 is a front cross-sectional view of a fifth alternative embodiment of the multi-lumen cannula of FIG. 1A.

FIG. 7 is a front cross-sectional view of a fifth alternative embodiment of the multi-lumen cannula 102a of FIG. 1A, referred to as sixth multi-lumen cannula 102f in FIG. 7. In the fifth multi-lumen cannula 102f, the supply/return catheter 106 and the evacuation line 108 are not concentric, and the fiber optic light distribution system 104 (not shown in FIG. 7) may be disposed within the supply/return catheter 106. For example, in the embodiment shown in FIG. 7, the supply/return catheter 106 and the evacuation line 108 are coupled together side-by-side. An additional supply/return catheter 106 and/or fiber housing line 112 may be similarly coupled to the supply/return catheter 106 and/or to the evacuation line 108 as shown in phantom by reference numerals 164a-b.

Operation of the inventive wound management system 100 of FIG. 1A will be described below with reference to FIG. 8 (which is a top plan view of one of the multi-lumen cannulas 102a-f within a wound 170). It will be understood that the inventive wound management system 100 may operate similarly regardless of which multi-lumen cannula 102a-f is employed. Accordingly, the operation of the wound management system 100 will be described generally with reference to a cannula 102 which may comprise any of the inventive cannulas 102a-f described herein.

Figure 8:
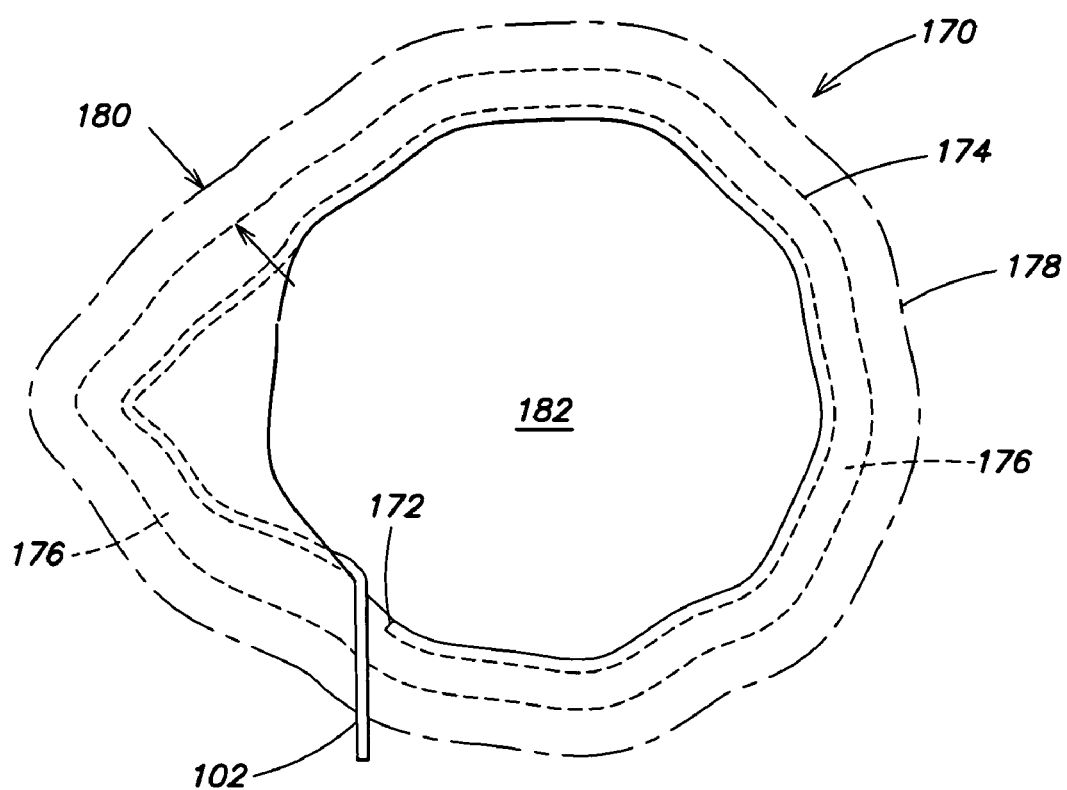
FIG. 8 is a top plan view of one of the multi-lumen cannulas of FIGS. 1A-7 within a wound.

With reference to FIG. 1A and FIG. 8, a distal end 172 of the cannula 102 is coiled around a perimeter 174 of the wound 170 and under any undermined sinus areas 176 of the wound 170. The wound 170 and cannula 102 then are sealed together using a suitable bandage 178 (shown in phantom). In at least one embodiment of the invention, the wound 170 and cannula 102 are sealed together using a double layer of TEGADERM™ clear plastic non-stretch bandage available from 3M. Other bandages or coverings also may be employed. The seal between a region 180 outside of the wound perimeter 174 (e.g., a debrided wound edge), such a portion of a patient's skin, and the cannula 102 and the bandage 178 preferably is gas and liquid tight relative to the wound cavity 182 so that all liquid and gas must travel through the cannula 102 to enter and/or leave the wound cavity 182.

As stated, the cannula 102 is "connected" to the controller 122 via the light source 116, the gas supply 118, the vacuum system 120 and/or the thermistor 110 (which may, for example, be implemented in a single bed side unit (not shown), or as part of a larger system). In one or more embodiments of the invention, the gas supply 118 may comprise a heated oxygen supply, and the vacuum system 120 may include a container (not shown) for collecting exudates and other liquids from the wound 170. The light source 116 may comprise, for example, a 5.0 Watt 630 nm Helium-Neon LASER, and an LED near infrared and ultraviolet array. Other gas and/or light sources may be employed.

In at least one embodiment of the invention, the controller 122 may be pre-set (e.g., programmed) or manually set to provide a specific sequence of hyper-thermic and/or hyperbaric gas (e.g., oxygen, nitric oxide, carbon dioxide, combinations thereof, etc.) exposures to the wound 170 which may be followed, for example, by a period of vacuum and/or fluid exudate evacuation. The sequences of gas exposures, time for gas exposure and/or evacuation, and/or other process parameters may be adjustable or fixed.

In one or more embodiments, the controller 122 may be configured so as not to permit over or under pressure wound environments, or light over-dosing. A series of mechanical pressure relief's and/or vacuum breakers (not shown) may be employed to further protect the wound environment.

The controller 122 may activate the light source 116 and may sequence the light source 116 as desired (e.g., for an adjustable time period during, for example, hyperbaric oxygen phase of the therapy). For example, UV-A frequency light is bactericidal to organisms, but has positive photosensitive properties with regard to human tissue (e.g., in low dosages). Likewise, 630 to 880 nanometer light has been shown to stimulate cell mitochondria, growth factors and micro-vasodilatation.

The light source 116 (e.g., via the controller 122) also may be employed to sterilize the wound 170 with UV radiation and/or provide growth inducing near infrared light into undermined wound tissue areas 176 via the fiber optic light distribution system 104. In general, the cannula 102 may operate with virtually any light source. In a bed-side unit embodiment of the invention (e.g., wherein the light source 116, the gas supply 118, the vacuum system 120 and/or the controller 122 are contained within a bedside unit (not shown)), the wound management system 100 typically will operate with a near infrared LASER or LED light source to promote healing. The system 100 also may accept (e.g., via a manual connection not shown) a controlled UV-B/C light source that may be employed to sterilize the wound 170 of pathogens. For example, a UV light source may be used in conjunction with antibiotics to eliminate pseutomosus bacteria or other pathogens.

In one or more embodiments of the invention, the gas supply 118 comprises a heated and variable medical oxygen supply that can deliver, for example, between about a 10 to 100 cc/minute oxygen flow at a maximum pressure of about 10 cm $H_2O$ into the wound site via the supply/return catheter 106. This may create a hyper-thermic (e.g., about 100-101° F.) and hyperbaric oxygen (e.g., about 5-10 cm $H_2O$) environment within the wound 170. Excess oxygen and wound liquid exudates are pushed up the evacuation line 108. Other flow rates, gas types, wound temperatures and/or gas pressures may be employed.

The controller 122 may periodically (or at any other time) increase vacuum (e.g., to 50 mm Hg or some other suitable vacuum level) to evacuate any exudate from the wound cavity 182, and/or to purge the wound cavity 182. During this variable evacuation period, the flow of gas (e.g., oxygen) may be increased (e.g., to about 100 cc per minute in one embodiment).

As stated, the cannula 102 may contain one or more other fluid delivery lines, such as an intervenes (IV) solution port that permits the injection of any liquid medication or saline flush. The controller 122 may be adapted to initiate such medication/saline flushes. Additionally, such medication/saline flushes may be performed through the supply/return catheter 106 and/or through the fiber housing line 112.

Embodiments of the present invention thus provide a comprehensive wound management system with multi-parameter control (e.g., via a microprocessor or the like) of inner wound environment of pressure ulcers, surgically induced wounds, other chronic wounds, traumatic injuries, etc., that can provide a near ideal balance of temperature, pressure, atmosphere, vasoconstriction/dilation, clot factors and/or bacteriostatic/bactericidal conditions necessary for optimized tissue granulation. Controlled delivery of fluids to and vacuum removal of fluids from a wound site allows drainage of secretions and maintenance of a wound tissue hyper-thermal environment with delivery of medications to the wound environment (without compromising the sterile wound dressing barrier). That is, a multi-function gas, liquid and light wound management system is provided that may deliver ultraviolet and near-infrared light under controlled, hyper-thermic and/or hyper/hypobaric wound conditions in accordance with one or more predefined protocols.

Figure 9A:
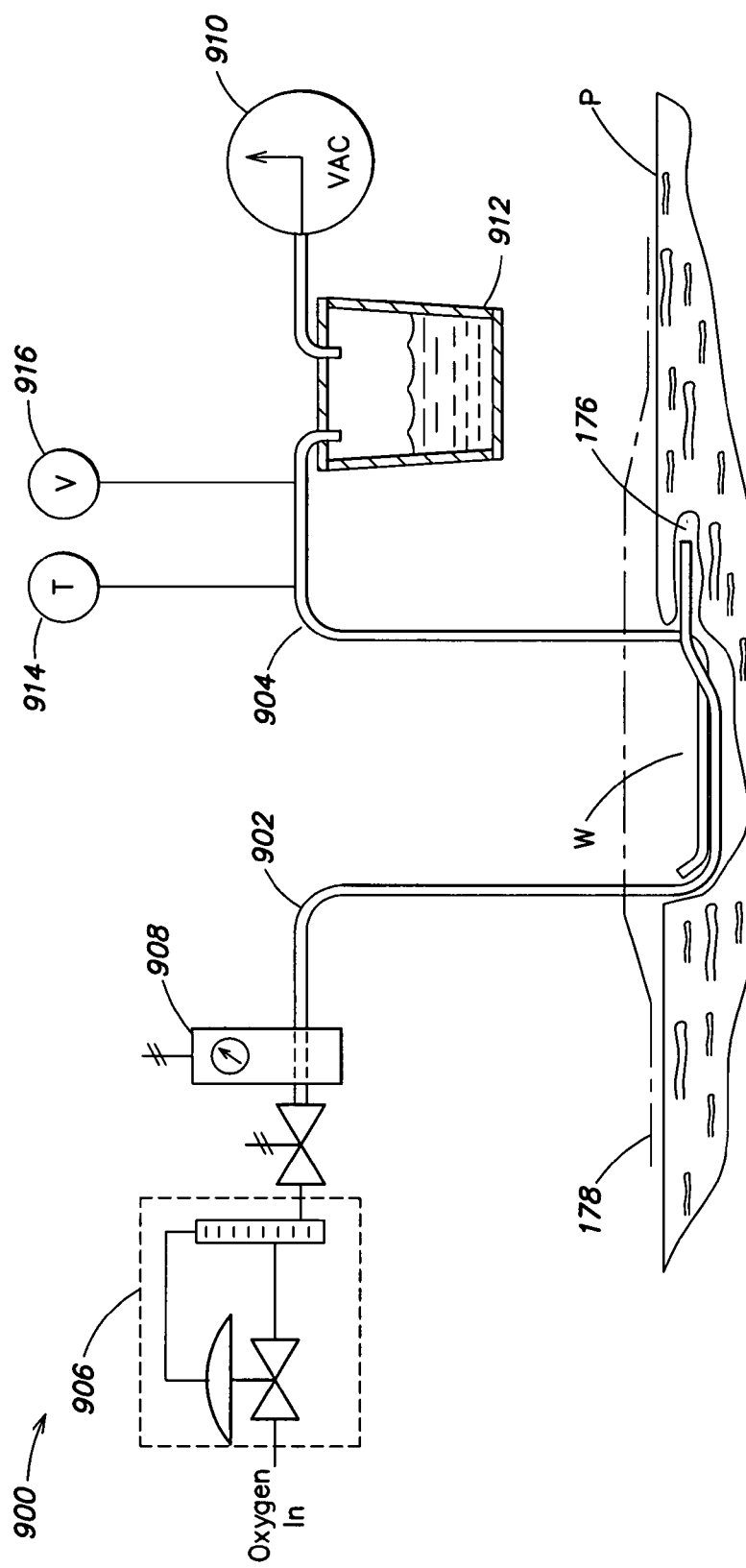
FIG. 9A is a schematic diagram of a second exemplary wound management system provided in accordance with the present invention.

FIG. 9A is a schematic diagram of a second exemplary wound management system 900 provided in accordance with the present invention. The wound management system 900 of FIG. 9A is similar to the wound management system 100 of FIG. 1A, but employs a supply line 902 that is separate from an evacuation line 904 of the system 900. In at least one embodiment of the invention, the wound management system 900 may include a pressure regulation system 906 that is adapted to provide a controlled pressure and/or flow rate of gas to a wound site W. The pressure regulation system 906 may operate, for example, similar to the gas flow control system 150 of FIG. 3B. For example, the pressure regulation system 906 may be employed to produce an oxygen or other gas flow rate of about 0.01 to 0.5 liters per minute, at a pressure of about 600-800 mmHg. Other flow rates and/or pressures may be employed.

Figure 9B:
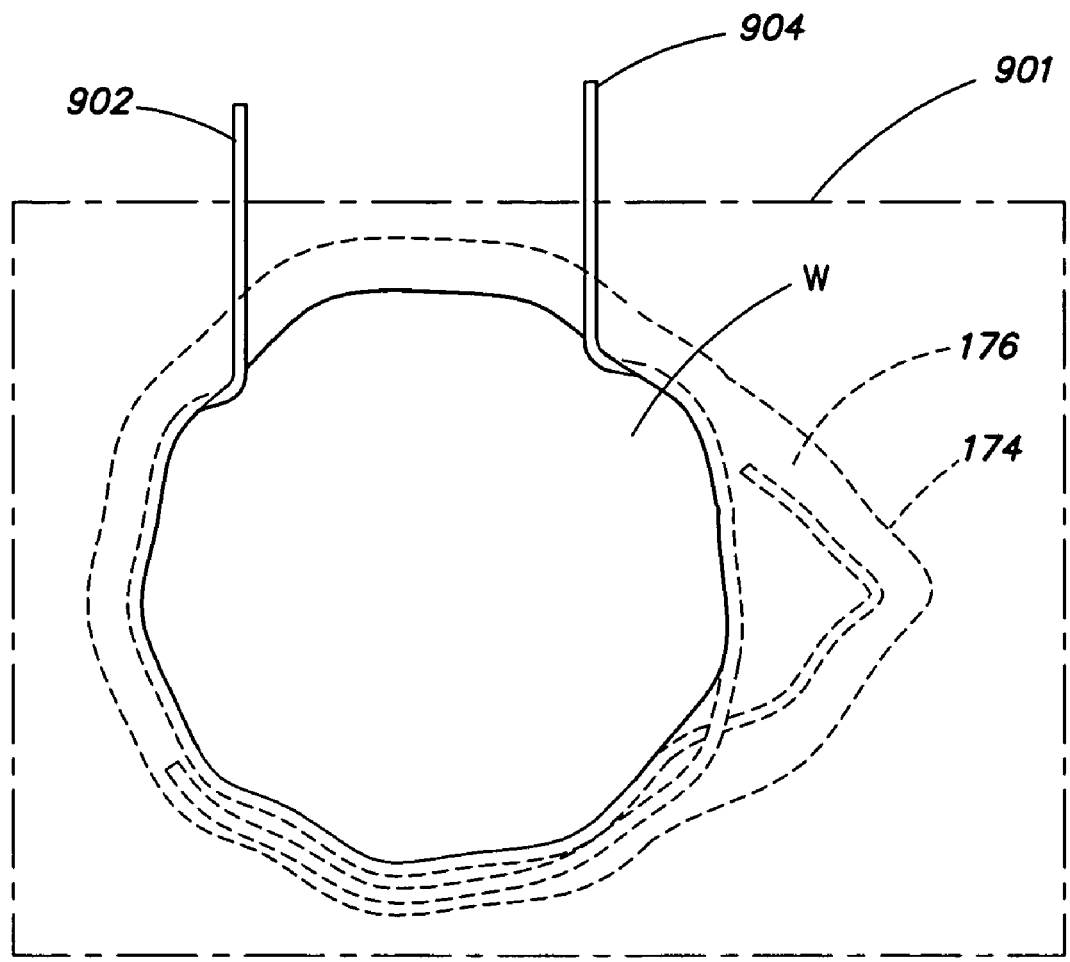
FIG. 9B is a top view of a portion of the wound management system of FIG. 9A within a wound site.

The wound management system 900 includes a heater unit 908, such as a resistive heater or the like (e.g., an oxygen heater), adapted to heat gas supplied from the pressure regulation system 906 prior to delivery to a wound site; and a vacuum system 910 adapted to create a negative pressure (e.g., a 600-700 mm vacuum) within a collection container 912 that is coupled to the evacuation line 904. Other negative pressures may be created. In this manner, a negative pressure may be maintained in the evacuation line 904 relative to the wound site W (e.g., of a patient P) so that exudates and other fluids may flow from the wound site W and be collected within the container 912. A temperature gage 914 and/or a vacuum gage 916 may be employed to measure the temperature and/or pressure of fluid within the evacuation line 904. The wound management system 900 may or may not include a light distribution system, such as the fiber optic light distribution system 104 of FIG. 1A, for delivering light doses to the wound sight W. The wound management system 900 also may include a controller (not shown) for controlling operation of the wound management system 900 in a manner similar to that described with reference to the wound management system 100 of FIG. 1A. FIG. 9B is a top view 901 of a portion of the wound management system 900 within the wound site W.

Figure 10A:
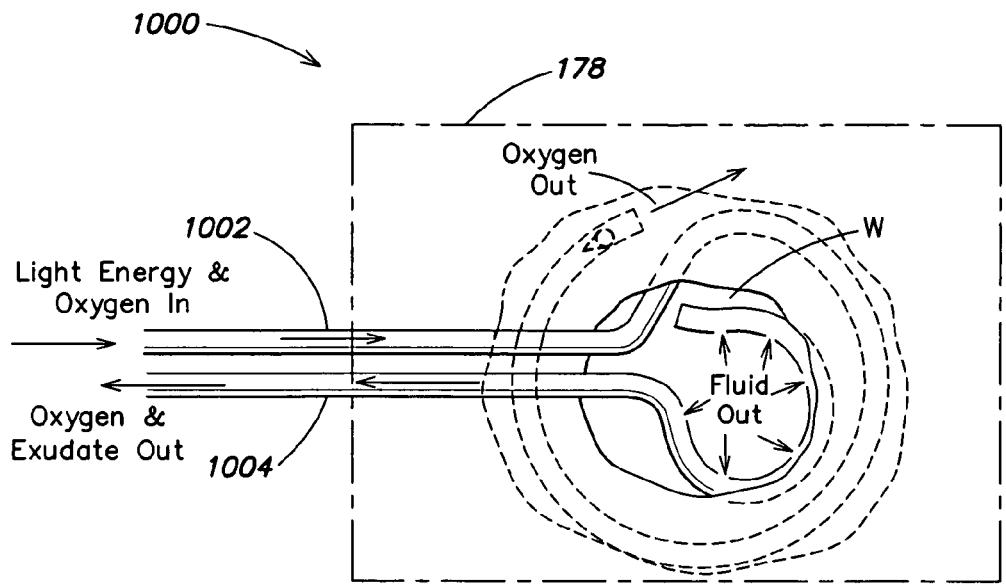
FIG. 10A is a schematic diagram of a third exemplary wound management system provided in accordance with the present invention.
Figure 10B:
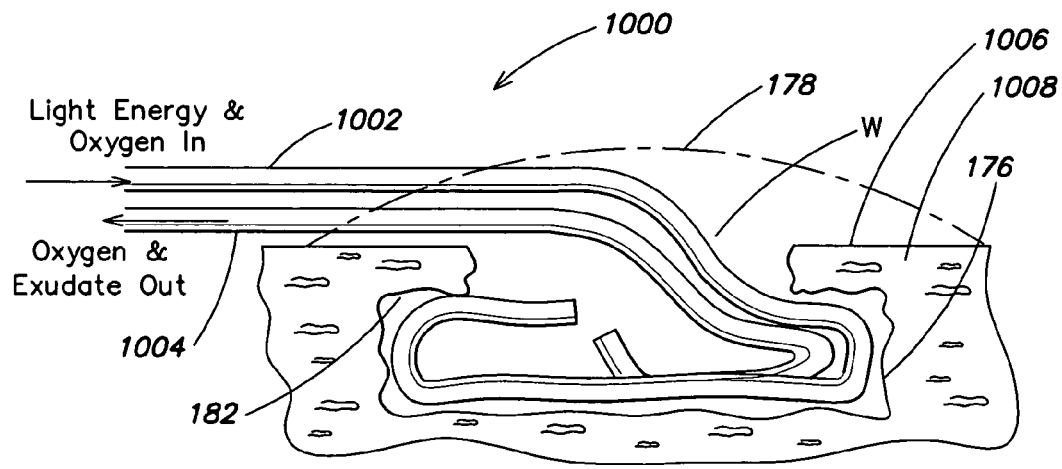
FIG. 10B is a top view of a portion of the wound management system of FIG. 10A within a wound site.

FIG. 10A is a schematic diagram of a third exemplary wound management system 1000 provided in accordance with the present invention. The wound management system 1000 of FIG. 10A is similar to the wound management system 100 of FIG. 1A, but employs a supply line 1002 that is separate from an evacuation line 1004 of the system 1000. The supply line 1002 may be employed to supply and/or strobe regulated light energy, such as ultraviolet and/or infrared light energy to a wound W. Further, the supply line 1002 may be employed to supply oxygen or other gasses into a wound cavity (e.g., disposed under a bandage 178). The evacuation line 1004 may be employed to vacuum remove oxygen and exudates from the wound cavity. FIG. 10B is a top view of a portion of the wound management system 1000 within the wound site W. A stage ¾ pressure wound is illustrated. However, the wound management system 1000 may be employed to treat other types of wounds. The wound W includes surface tissue 1006 over a transdermal wound area 1008. In one embodiment of the invention, the supply line 1002 is employed to provide light via fiber optics and/or oxygen to the wound cavity and the evacuation line 1004 is employed to remove exudate fluid from the wound cavity 182, which may include an undermining cavity (e.g., an undermined sinus area 176), by creating a pressure of −20/50 mm Hg.

Figure 10C:
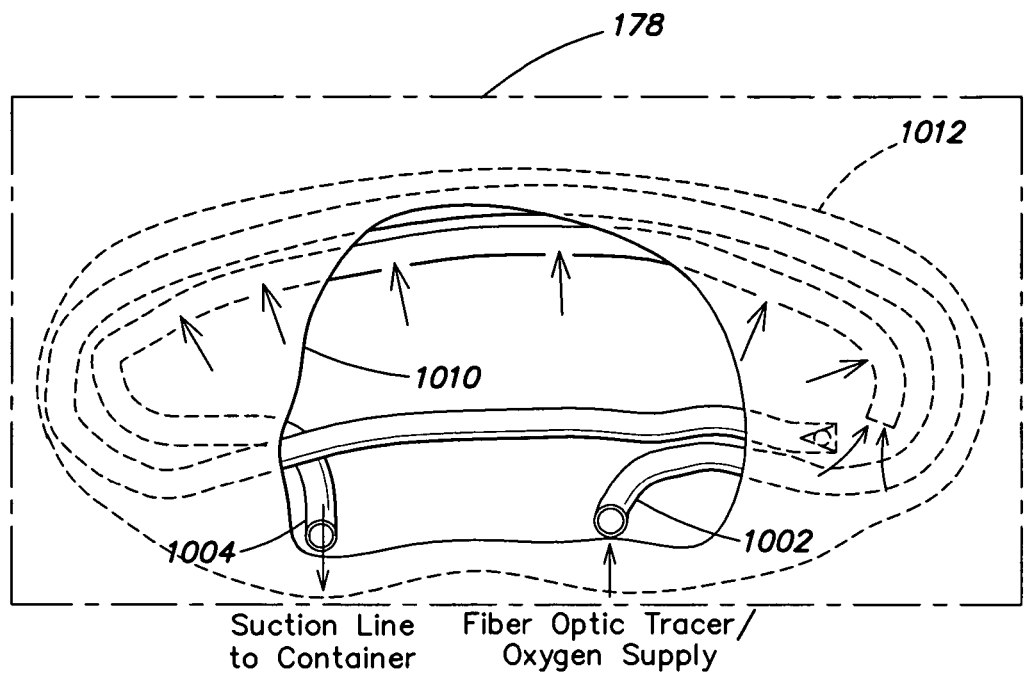
FIG. 10C is a schematic diagram of an alternative embodiment of the third exemplary wound management system of FIG. 10A.
Figure 10D:
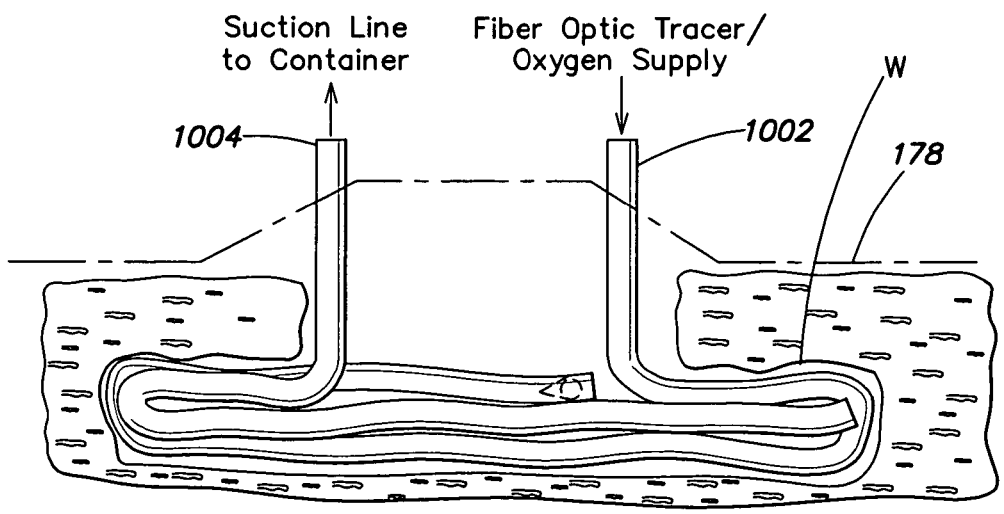
FIG. 10D is a top view of a portion of the wound management system of FIG. 10C within a wound site.

FIG. 10C is a schematic diagram of an alternative embodiment of the third exemplary wound management system 1000 of FIG. 10A; and FIG. 10D is a top view of a portion of the wound management system 1000 within the wound site W. The wound site W includes a surface wound opening area 1010 and an undermined wound perimeter 1012 (e.g., an undermined sinus area perimeter). In at least one embodiment of the invention, the pressure maintained within the wound site W by the wound management system 1000 is approximately +20 cm $H_2O$. For example, the pressure of the gas delivered to the wound site W via the supply line 1002 may be about +10 cm $H_2O$ and the pressure in the wound site may be about +10 cm $H_2O$ (e.g., with a movement of about 10 cc/sec of exudates/fluid via the evacuation line 1004). Other pressures/flow rates may be employed. In one embodiment of the invention, the evacuation line 1004 is operated at a pressure of about 50 mmHg. Other pressures may be created by the evacuation line 1004.

The foregoing description discloses only exemplary embodiments of the invention. Modifications of the above disclosed apparatus and methods which fall within the scope of the invention will be readily apparent to those of ordinary skill in the art. For instance, other pressures, temperatures, gases, light frequencies, flow rates, irrigation fluids than those described herein may be employed. Other catheter/line diameters may be employed. The supply/return catheter 106 and/or the fiber housing line 112 may have an outer diameter of between about 1/32 and 1/8 inch in one or more embodiments.

While the present invention has been described with reference to chronic wounds such as decubitus, ischial and sacral ulcers, it will be understood that the invention may be employed to treat virtually any wound. Other techniques for delivering light to a wound site may be employed in place of, or in addition to, the fiber optic light distribution system 104.

In one embodiment, the light source 116 may include ultraviolet (UV) and near infrared light sources. For example, the light source 116 may include UV-A, UV-B, UV-C bands and/or a 300-900 nm bandwidth infrared frequency transmission. Other types of light sources may be employed.

As used herein, a fluid may include a gas or a liquid.

Accordingly, while the present invention has been disclosed in connection with exemplary embodiments thereof, it should be understood that other embodiments may fall within the spirit and scope of the invention, as defined by the following claims.

The invention claimed is:

1. A method of treating a wound site comprising:
   providing a multi-lumen cannula having:
      a fiber optic light distribution system adapted to irradiate the wound site with light;
      one or more catheters adapted to deliver a fluid to the wound site; and
      one or more evacuation lines adapted to remove fluid from the wound site;
   disposing the multi-lumen cannula in the wound site; and
   treating the wound site using the multi-lumen cannula,
   wherein treating the wound site comprises delivering a dose of light to the wound site having a wavelength ranging from about 350 to 900 nanometers.

2. The method of claim 1 wherein treating the wound site further comprises maintaining a hyperbaric pressure at the wound site.

3. The method of claim 1 wherein treating the wound site further comprises delivering at least one of medication and a saline flush to the wound site.

4. The method of claim 1 wherein treating the wound site further comprises removing exudates from the wound site.

5. The method of claim 1 wherein treating the wound site further comprises heating the wound site.

* * * * *